US010849772B2

United States Patent
Liungman

(10) Patent No.: US 10,849,772 B2
(45) Date of Patent: Dec. 1, 2020

(54) METHOD OF RETRIEVING A RETRIEVABLE DEVICE AND AN ASSEMBLY OF THE RETRIEVABLE DEVICE AND A RETRIEVING ELEMENT

(71) Applicant: Endovascular Development AB, Uppsala (SE)

(72) Inventor: Krister Liungman, Uppsala (SE)

(73) Assignee: ENDOVASCULAR DEVELOPMENT AB, Uppsala (SE)

( * ) Notice: Subject to any disclaimer, the term of this patent is extended or adjusted under 35 U.S.C. 154(b) by 532 days.

(21) Appl. No.: 14/892,469

(22) PCT Filed: May 22, 2014

(86) PCT No.: PCT/EP2014/060570
§ 371 (c)(1),
(2) Date: Nov. 19, 2015

(87) PCT Pub. No.: WO2014/187913
PCT Pub. Date: Nov. 27, 2014

(65) Prior Publication Data
US 2016/0106563 A1    Apr. 21, 2016

(30) Foreign Application Priority Data
May 22, 2013   (DK) .................................. 2013 70271

(51) Int. Cl.
*A61F 2/95* (2013.01)
*A61B 17/12* (2006.01)
*A61F 2/01* (2006.01)

(52) U.S. Cl.
CPC ...... *A61F 2/95* (2013.01); *A61B 2017/12054* (2013.01); *A61F 2/011* (2020.05);
(Continued)

(58) Field of Classification Search
CPC ................ A61F 2/95; A61F 2230/0091; A61F 2002/9529; A61F 2002/011;
(Continued)

(56) References Cited

U.S. PATENT DOCUMENTS 5,312,415 A * 5/1994 Palermo ........... A61B 17/12022
606/108
5,725,546 A * 3/1998 Samson ........... A61B 17/12022
606/191
(Continued)

FOREIGN PATENT DOCUMENTS

CA     2613117 A1   5/2001
EP     1120088 A1   8/2001
(Continued)

OTHER PUBLICATIONS

Danish Search Report for Application No. PA 201370271 dated Nov. 28, 2013.
(Continued)

*Primary Examiner* — Erich G Herbermann
(74) *Attorney, Agent, or Firm* — Harness, Dickey & Pierce, P.L.C.

(57) ABSTRACT

An assembly of a retrieving element and a retrievable device of which one is a helical spring having an outer part of a winding which extends away from a main portion of the spring and thus is able to engage a thread of the other of the retrieving element and a retrievable device. The other of the retrieving element and a retrievable device may have an outer or an inner thread. The assembly may be used for retrieving devices temporarily positioned in a blood vessel of a person.

22 Claims, 4 Drawing Sheets

Figure 1:
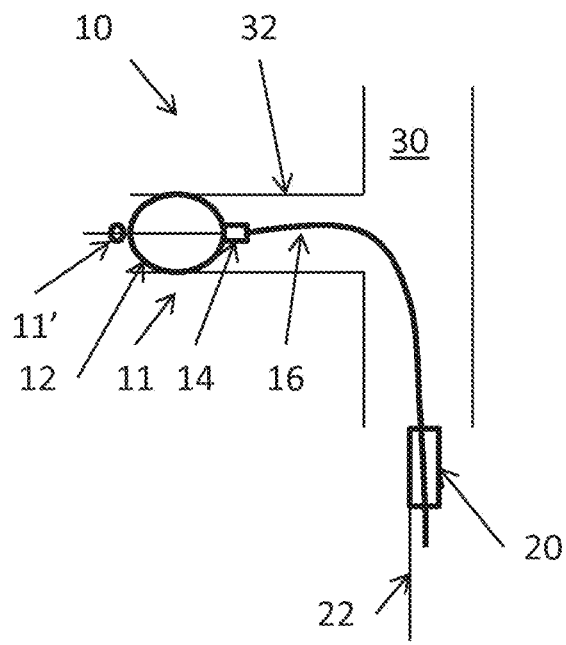

(52) U.S. Cl.
CPC ............... *A61F 2002/9505* (2013.01); *A61F 2002/9528* (2013.01); *A61F 2230/0091* (2013.01)

(58) Field of Classification Search
CPC ..... A61F 2002/9505; A61F 2002/9528; A61B 2017/12054
See application file for complete search history.

(56) References Cited

U.S. PATENT DOCUMENTS

| | | | |
|---|---|---|---|
| 6,371,971 | B1 | 4/2002 | Tsugita et al. |
| 6,969,395 | B2 | 11/2005 | Eskuri |
| 7,316,655 | B2 | 1/2008 | Garibotto et al. |
| 7,776,062 | B2 | 8/2010 | Besselink et al. |
| 2004/0220610 | A1* | 11/2004 | Kreidler ............. A61B 17/0057 606/200 |
| 2006/0129180 | A1 | 6/2006 | Tsugita et al. |
| 2007/0255386 | A1 | 11/2007 | Tenne |
| 2008/0045997 | A1* | 2/2008 | Balgobin ......... A61B 17/12022 606/200 |
| 2008/0119889 | A1 | 5/2008 | Kusleika |
| 2009/0318951 | A1 | 12/2009 | Kashkarov et al. |
| 2009/0326551 | A1 | 12/2009 | Drake et al. |
| 2010/0152769 | A1 | 6/2010 | Gesswein et al. |
| 2012/0123510 | A1 | 5/2012 | Liungman |
| 2014/0163665 | A1 | 6/2014 | Tenne |

FOREIGN PATENT DOCUMENTS

| | | |
|---|---|---|
| WO | WO-9600104 A1 | 1/1996 |
| WO | WO-2005105191 A2 | 11/2005 |
| WO | WO-2007079410 A2 | 7/2007 |
| WO | WO-2012065625 A1 | 5/2012 |

OTHER PUBLICATIONS

International Search Report PCT/ISA/210 for International Application No. PCT/EP2014/060570 dated Aug. 22, 2014.

Written Opinion of the International Searching Authority PCT/ISA/237 for International Application No. PCT/EP2014/060570 dated Aug. 22, 2014.

* cited by examiner

METHOD OF RETRIEVING A RETRIEVABLE DEVICE AND AN ASSEMBLY OF THE RETRIEVABLE DEVICE AND A RETRIEVING ELEMENT

CROSS-REFERENCE TO RELATED APPLICATIONS

This application is a national phase under 35 U.S.C. § 371 of PCT International Application No. PCT/EP2014/060570 which has an International filing date of May 22, 2014, which claims priority to Dannish Application No. PA 2013 70271 filed May 22, 2013, the entire contents of each of which are hereby incorporated by reference.

The present invention relates to a method of retrieving a retrievable device and an assembly of a device and a retrieving element. In particular, the retrievable device may be a device for temporary positioning into a blood vessel of a person. Devices of this type may be intravascular filters, anchors, dilators, stents, grafts or the like.

Retrievable devices may be found in e.g. US2007/255386, WO96/00104, US2009/0326551, U.S. Pat. Nos. 6,969,395, 6,371,971, US2008/0119889, U.S. Pat. No. 7,316,655, US2010/0152769, US2006/0129180, U.S. Pat. No. 7,776,062, WO2005/105191, CA2613117, WO2012/065625 and U.S. Pat. No. 6,371,971. Also known is the Amplatzer plug for occlusion of a blood vessel as well as various emboli protection filters used during carotid artery stenting, devices for positioning and closure between the left and right atrium or left and right chambers of the heart.

In a first aspect, the invention relates to an assembly of a retrieving element and a retrievable device, wherein:
the retrievable device has one of:
a male element having a first, outer, surface part defining a first thread having a predetermined direction of rotation around a longitudinal axis of the male element, and
a female element having a second, inner, surface part defining a second thread configured to mate with the first thread, the second thread having the predetermined direction of rotation around a longitudinal axis of the female element,
the retrieving element has the other of the male element and the female element,
wherein at least one of the male element and the female element has a main part and a protruding part protruding from the main part, the main part having the surface part defining the pertaining first or second thread, the protruding part extending at least partly around the longitudinal axis of the pertaining male or female part and away from the main part, the direction of rotation of the protruding part being the same as the direction of rotation of the pertaining first or second thread of the pertaining male or female part.

In this context, an assembly is a combination of multiple parts or a number of combinable parts. In this context, the assembly comprises a retrievable device and a retrieving element. Additional elements or parts may be provided.

A female element is an element configured to receive therein another element—the male element. Usually, the male element will engage the female element when introduced therein. In the present context, the male element and the female element comprise threads which are preferably configured to engage so that the male element may not be removed from the female element by simple translation but where a rotation of the male element in relation to the female element may bring about attachment or detachment/removal. This is typically the situation when the threads of both the male and female elements have ridges and valleys where the ridges (first radius in a cross sectional plane perpendicular to the longitudinal axis) of the male element extend between the ridges of the female element (second radius), so that the first radius is larger than the second radius.

Usually, a thread of a screw/bolt (male element) or a nut (female element) is defined as e.g.: a helical or spiral ridge on a screw, nut, or bolt, such as a helical groove in a cylindrical hole (female thread), formed by a tap or lathe tool, or a helical ridge on a cylindrical bar, rod, shank, etc. (male thread), formed by a die or lathe tool. Another definition may be: a screw thread, often shortened to thread, is a helical structure used to convert between rotational and linear movement or force. A screw thread is a ridge wrapped around a cylinder or cone in the form of a helix, with the former being called a straight thread and the latter called a tapered thread. A screw thread is the essential feature of the screw as a simple machine and also as a fastener. The mechanical advantage of a screw thread depends on its lead or pitch, which is the linear distance the screw travels in one revolution. In most applications, the lead of a screw thread is chosen so that friction is sufficient to prevent linear motion being converted to rotary motion, that is, so the screw does not slip even when linear force is applied so long as no external rotational force is present. This characteristic is essential to the vast majority of its uses. The tightening of a fastener's screw thread is comparable to driving a wedge into a gap until it sticks fast through friction and slight plastic deformation. Alternatively, a tactile feedback may be provided.

Usually, the thread of the male and female elements will have about the same radius (of the lowest parts of the valleys and the highest parts of the ridges, respectively) along their longitudinal axes, but this is not a requirement. A change in radius may be desired to obtain a higher and lower engagement so as to e.g. obtain a type of locking, when a sufficient rotation has been achieved.

The rotation around the longitudinal axis is either clockwise or counterclockwise in the direction from the pertaining male/female element toward the other male/female element.

In general, the retrieving element is configured to engage, via the threads, the retrievable device, irrespective of where the retrievable device is situated and what functionality the retrievable device has. In an interesting embodiment, the retrievable element is configured to be used in rather narrow channels, such as human blood vessels, which are rather vulnerable and in addition typically may have sharp bends.

The retrieving element therefore preferably is configured to retrieve and/or engage the retrievable device even when an angle exists between the longitudinal axes thereof.

Usually, the lead of the first and second threads is the same, and preferably, the lead of the first and second threads is the same along the longitudinal axes.

In addition to the first/second thread, one of the male and female elements has a protruding part. The one of the male/female element has the first or second thread which is provided on or as a part of a main part thereof. The protruding part protrudes from the main part and may be a monolithic part thereof or may be fixed thereto or otherwise engage the main part.

The protruding part extends away from the main part and at the same time at least partly around the longitudinal axis with a direction of rotation around the longitudinal axis as the direction of rotation of the pertaining first or second thread of the pertaining male or female part. In a preferred embodiment, the protruding part will define one or more ridges and/or valleys or a surface part which may extend the thread of the main part.

The advantage of the protruding part is that it protrudes from the main part having the thread. Thus, the protruding part may grip or engage the other of the male and female element from an angle, between a longitudinal axis of the main part and a longitudinal axis of the other of the male and female element, of at least 10 degrees, such as at least 20 degrees, such as at least 30 degrees, such as at least 40 degrees, such as at least 50 degrees, such as at least 60 degrees, such as at least 70 degrees, such as at least 80 degrees.

Usually, when threads are to engage, the longitudinal axes need to be aligned. It is preferred that the first and second threads are able to be brought to engagement even if the longitudinal axes of the retrieving element and retrievable device are at an angle.

It has been found that a protruding part will be able to catch the other of the male/female part. The protruding part preferably protrudes so that a tip thereof and an outer part of the main part opposite, in relation to the longitudinal axis, to the tip, define a line having an axis of no more than 80 degrees to the longitudinal axis, such as no more than 70 degrees, such as no more than 60 degrees, such as no more than 50 degrees, such as no more than 45 degrees.

Thus, a plane may be defined comprising the tip of the protruding part, the opposite part and the longitudinal axis. Another plane may be defined perpendicular to this plane and also comprising the tip and the opposite part. Preferably, no large part, such as no part, of the pertaining male or female element extends to the other side of this other plane.

Also, it is preferred that the protruding part extends, in a cross section perpendicular to the longitudinal axis, in a radial direction toward/from the longitudinal axis, no more than 50% of an outer radius of the thread of the main part, such as no more than 45%, such as no more than 40%, such as no more than 35%, such as no more than 30%, such as no more than 25%, such as no more than 20%, such as no more than 15%. When the protruding part is rather slim, it allows a space into which parts of the other of the element/device may travel so as to allow the protruding part to engage the thread thereof in the situation where an angle exists between the two longitudinal axes.

This angle and plane will define the angle under which the other of the male/female element may approach the protruding portion, where no other part of the pertaining male/female element will be able to interfere with the engagement.

Due to the fact that the protruding portion extends both away from the main portion and around the longitudinal axis, rotation of the pertaining male/female element will keep the engagement while bringing the two elements closer to each other. Finally, the first and second threads will be able to engage.

Naturally, the concept of a male and a female part may be expanded, so that inner and outer threads may be used as well as a channel. Threads of any type may be used.

In one embodiment, the male element has the protruding part and the first outer surface extends no more than a first, predetermined distance from the longitudinal axis of the male element, and the protruding part extends no more than the first predetermined distance from the longitudinal axis. Thus, when the protruding part extends no further from the longitudinal axis, it will not interfere with the engagement of the threads. The protruding part may be provided closer to the longitudinal axis than the first thread. In that situation, the protruding part may simply disengage the second thread, when the first and second threads engage.

In another embodiment, the female element has the protruding part and the second outer surface extends at least a second, predetermined distance from the longitudinal axis of the female element, and wherein the protruding part extends at least the second predetermined distance from the longitudinal axis. In this situation, the protruding part may extend farther from the longitudinal axis, whereby it may disengage the first thread, when the first and second threads engage.

In one embodiment, the protruding part has a tip portion extending the farthest from the main part, the tip portion extending at least ¼ of a lead/pitch of the thread of the pertaining first or second threads, such as at least ⅓ of the lead, such as around ½ of the lead.

As the above angle, the size of the protruding part will have an effect on the maximum angle difference between the longitudinal axes, where the protruding element can nevertheless catch the other of the male and female element.

In an interesting embodiment, the main part is flexible or bendable, so that, when the protruding part engages the other of the male/female element, the main part may bend so as to reduce the angular difference between the 'effective' longitudinal axes of the male and female elements in that the parts of the flexible part the closest to the other part, due to a deformation of the flexible part, may be at a lower angle than a remaining part thereof. This flexibility or bendability will depend heavily on the sizes of the elements.

Preferably, the protruding part has a surface part continuing the thread of the main part. Thus, the protruding part may have a surface part defining a ridge or convex part and may be positioned, in relation to the main part, so as to extend a ridge of the main part. Preferably, the protruding part also is shaped so that the lead of the thread of the main part is continued or is the same.

In a particular embodiment, the at least one of the male and female element comprises a helical coil, such as a helical spring, the protruding part being a part of an extreme or outer winding of the coil and the main part forming part of a central portion of the spring. Thus, the outer part of the winding may have the same lead/pitch and extend away from the remainder of the spring so as to form a protruding part. In addition, springs are bendable or deformable, so that the main part, formed by a part of the spring, may be bent as well. Springs/coils may form outer or inner threads and thus may form a male or female part.

In one embodiment, the retrievable device comprises a guidewire extending to, such as attached at or to, the male or female element of the retrievable element, the guidewire extending through, such as along the longitudinal axis of, the male or female element of the retrieving element. Thus, the retrieving element may have a channel or the like receiving the guidewire, whereby advancing the retrieving element along the guidewire will bring the retrievable device and the retrieving element in close proximity. Also, the operation of the guidewire may be to provide a certain alignment of the longitudinal axes of the retrievable device and the retrieving element, so that the protruding element may perform its operation. In the situation where the retrieving element is a coil, the guidewire may extend through the coil.

In one embodiment, the retrievable device comprises a compressible element configured to be provided inside a blood vessel of a person or animal, the compressible element being compressible to a diameter, for example, not exceeding 2 times an outer diameter of the female element. An example of a compressible element may be an anchor as seen in e.g. WO2012/065625. In this situation, where the retrieving element comprises the coiled spring, the assembly could further comprise a hollow, elongated element configured to receive therein the male and female elements, the female element comprising the helical coil, the helical coil being a coiled, elongate element having a predetermined, smallest diameter, the male element comprising a thread with one or more groove(s) and one or more ridge(s), an inner diameter of the hollow, elongate element smaller than the predetermined smallest diameter plus an outer diameter of the male element, when projected on to a plane perpendicular to a longitudinal axis of the male element. In this situation, when the male and female elements are provided inside the elongate element, the threads cannot disengage by translation, so that when relative rotation is prevented, disengagement is not possible.

In the situation where the elongate element has a diameter, d, exceeding the groove depth, the inner diameter of the hollow, elongated element may be chosen so that the inner diameter of the hollow, elongate element smaller than 2*d+H−h, where:

h is a depth of the groove(s), and
H is an outer diameter of the male element, when projected on to a plane perpendicular to a longitudinal axis of the male element.

In one embodiment, the male and female parts are configured to provide a tactile feedback when the first and second threads have been rotated, in relation to each other, a predetermined angle. This tactile feedback may be a rotation stop, when the end of a thread has been reached or when abutting surfaces of the male and female elements, respectively, abut, so that an operator will know that further rotation is not required or possible.

Another aspect of the invention relates to a method of operating the assembly according to the first aspect, the method comprising:

advancing the retrieving element toward the retrievable device,
  rotating the retrieving element in relation to the retrievable device to have the protruding portion engage the thread of the other of the male and female elements, and
  maintaining rotation to have the first and second threads engage.

The advancing step may be a translation step. Rotation may not be desired or efficient, as long as a distance exists between the retrievable device and retrieving element. The advancing step may be performed by pushing or guiding the retrieving element toward the retrievable device.

The rotating step may comprise the protruding part engaging the thread of the other of the element/device, where further rotation then may bring the protruding part further along the thread and thus the element closer to the device. This bringing closer may bring about an alignment of the longitudinal axes and the approaching of the threads of the element and device.

When the protruding part is an extension of the thread of the pertaining element/device, further rotation may bring the actual thread of the element/device having the protruding part into contact with the thread of the other of the element and device.

It is noted that the protruding part may have a point part which is the first to engage the thread of the other of the element/device and that this engagement may take place even if an angle exists between the longitudinal axes of the (threads of) element and device. Further rotation may maintain this tip portion in engagement with the thread, but the main part may engage the other of the element/device and thus operate to align the longitudinal axes (completely or at least more) so that the threads may engage.

Preferably, the method comprises, during at least the step of maintained rotation, the step of maintaining the protruding part in engagement with the thread of the other of the element/device so as to obtain the reduction in distance and the alignment of the axes. Thus, a force may be exerted on the protruding part toward the thread.

This step may be obtained using the below and above mentioned guidewire, which will act to prevent the protruding part from disengaging the thread, but other manners also exist of exerting this force.

In one embodiment, the retrievable device is an intravascular element, such as a graft, a filter, an anchor or the like, whereby the guiding may be as usual in endovascular techniques using steerable guidewires/catheters and the like.

The rotation is relative but is preferably performed by rotating the retrieving element. In one situation, the retrieving element is controllable and the retrievable element not or it is not desired to control the retrievable element, so that the advancing and rotation is performed by the retrieving element.

In one situation, the retrievable device comprises a guidewire leading toward the retrievable device and wherein the retrieving element comprises an opening through which the guidewire is translated to guide the retrieving element toward the retrievable element. Thus, the advancing step is performed by advancing the retrieving element along the guidewire. As mentioned further above, even though the guidewire may guide the retrieving element toward the retrievable device, an angle may still exist between the longitudinal axes of the device/element, whereby the operation of the protruding part is to engage the other of the element/device and, during rotation, align the longitudinal axes more, so that the threads of the element/device may engage.

In one situation, the advancing step comprises simply advancing the retrieving element until it abuts the retrievable device. There after, the rotation may be initiated, for example.

The final step of maintaining the rotation may be performed for a predetermined number of revolutions or until a tactile rotation stop has been encountered.

The finally engaging element/device are now attached to each other, and this engagement or attachment may be used for multiple purposes, such as a re-positioning of the retrievable device by operation (pulling, pushing, guiding for example) via the retrieving element.

The retrievable device may simply be moved or may be operated to be dislodged from a position by e.g. forcing, such as by pulling the retrieving element, the retrievable device into a catheter or tube guided toward the retrievable device by the retrieving element or e.g. a guidewire or control rod connected to the retrieving element. This pulling of the retrievable device into the catheter/tube may bring about a compression or cross-sectional reduction of the retrievable device so that dislodgement occurs and a repositioning is possible.

Naturally, this assembly and method may be used in a number of manners, as it primarily relates to a manner of engaging two threaded elements where a difference/angle may exist between the longitudinal axes thereof.

Another situation is the engagement, in narrow surroundings, of a screw and a nut. In this situation, the protruding part may also aid in the connection, as it may be difficult to completely align a standard screw and bolt in narrow surroundings, where it is difficult to e.g. manipulate the elements by hand.

Figure 2:
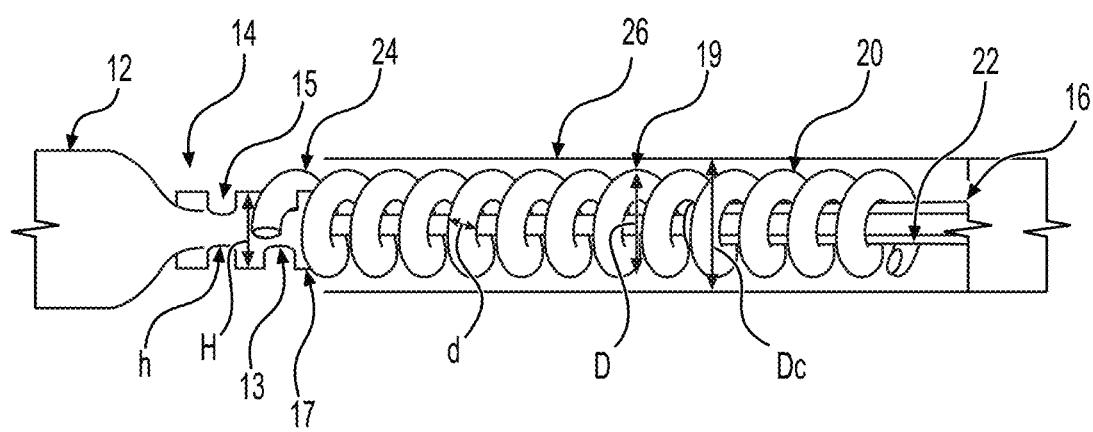
Figure 3:
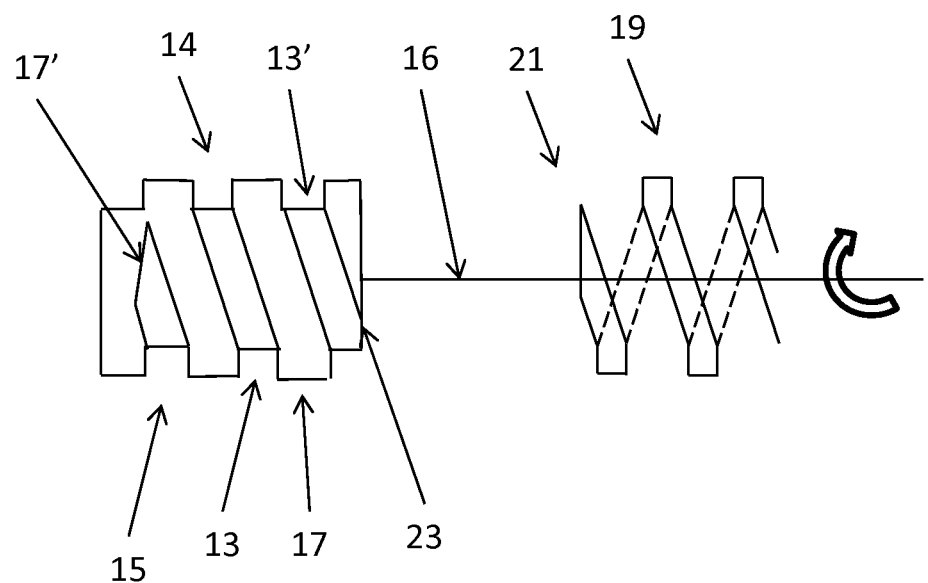
Figure 4:
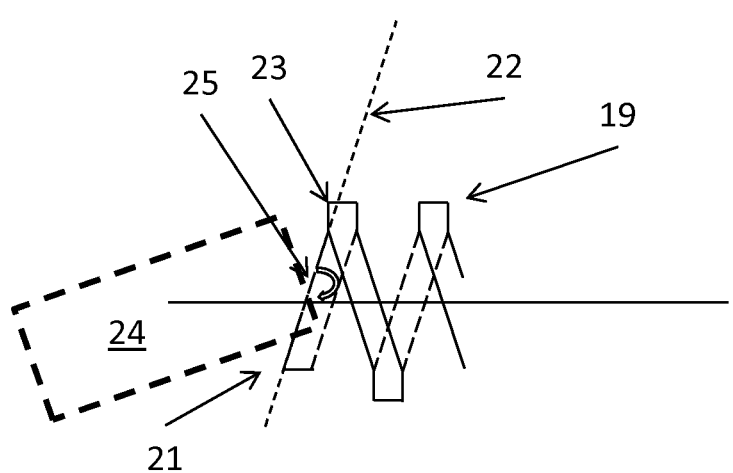
Figure 5:
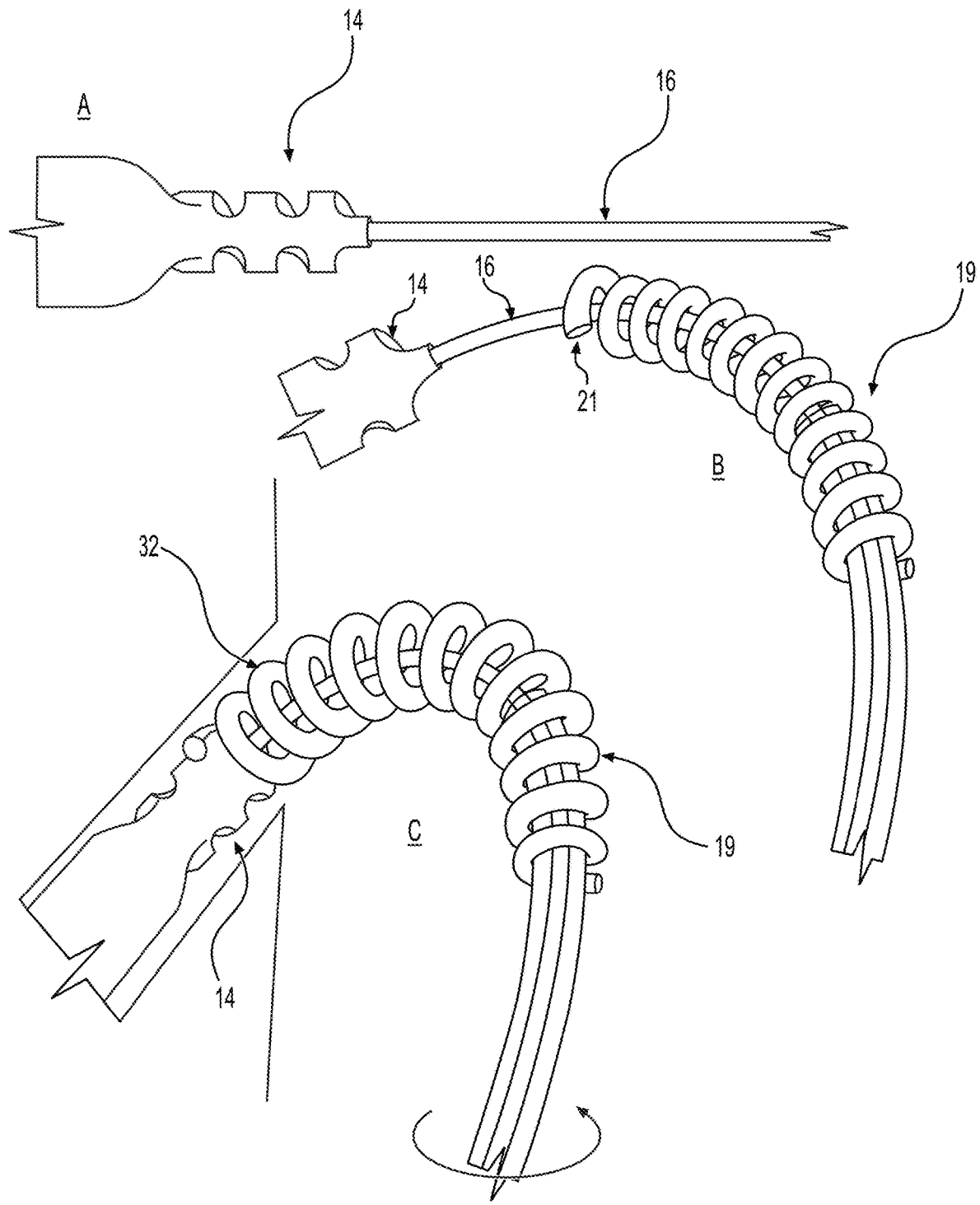

In the following, preferred embodiments will be described with reference to the drawing, wherein:

FIG. 1 is an overall illustration of a use scenario using an assembly according to the invention, FIG. 2 illustrates operation of a preferred embodiment of the assembly of the invention, FIG. 3 further illustrates the operation of the embodiment of FIG. 2, FIG. 4 illustrates the spring of FIG. 3 from another angle, FIG. 5 is a 3D illustration of the use of the assembly of FIG. 1, In FIG. 1, a fixator 11 as that seen in WO2012/065625, which is hereby incorporated by reference, is illustrated which is positioned in a side branch 32 of a main blood vessel 30, such as the aorta of a person or animal.

The fixator 11 has an expandable/collapsible basket 12 which is configured to fix itself temporarily to the side branch 32 during an endovascular procedure, such as the providing and positioning of a graft in the main blood vessel 30 with a fenestration or branch at the entrance or into the side branch 32.

The fixator 11 has a guidewire 16 attached thereto for numerous purposes, such as for guiding the abovementioned graft (not illustrated) through a fenestration or branch thereof.

Preferably, this guidewire 16 extends to outside the person so that it may be used for engaging the device to be guided already outside the person.

The guidewire 16 is attached to the fixator 11 in a manner so that it has a stopping element 11' attached to the guidewire 16 and which is prevented from moving proximally of a distal end of the basket 12. Thus, this prevents withdrawal of the guidewire 16 from the fixator 11. However, it allows guidewire 16 to be moved distally in relation to the fixator 11. Also, pulling the guidewire 16 (proximally) will force the stopping element 11' in the proximal direction and thus cause the fixator 11 to expand and thus fix itself even better to the branch 32.

In order to be able to retrieve the fixator 11 or re-position the fixator 11, it has an engagement element 14 connected to a proximal end of the basket 12 and from which the guidewire 16 extends proximally toward the operator.

In addition, a retrieval device 20 is illustrated through which the guidewire 16 extends so that the retrieval device 20 is guided by the guidewire 16 toward the fixator 11 and the engagement element 14. It is noted that guiding by the guidewire 16 does not require the guidewire 16 extending through the retrieval device. Also, it is noted that the guiding by the guidewire 16 is a preferred embodiment only. Other manners exist of reaching an element inside a blood vessel, such as the use of radiopaque markers or contrast guidance and the like.

The retrieval device 20 is controlled and advanced using a controlling device 22 which may be a catheter or the like as is known in the art. The controlling device 22 preferably is configured to translate the retrieval device 20 along the guidewire 16 and to, c.f. further below, rotate the retrieval device 20 in relation to the engagement element 14 so as to interlock the retrieval device 20 and the engagement element 14.

In FIG. 2, a preferred type of retrieval device 20 and engagement element 14 are illustrated. The preferred retrieval device 20 is a coiled spring 19 mounted over or onto a hollow catheter forming the controlling device 22 and through which the guidewire 16 travels. This catheter is not a requirement as the guidewire 16 may simply travel through the coil 19, or the catheter may be mounted in different manners in relation to the spring, such as at an end thereof.

The engagement element 14 is a moulded element having ridges 17 and valleys 13 forming a thread 15 corresponding to the turns (pitch etc.) of the coil 19, so that the coil 19, when rotated, engages the thread 15 in the same manner as a nut and bolt.

The operation and advantages of especially the helical spring/coil 19 will be described further below.

In FIG. 2, illustrated is also an outer catheter 26 which may be advanced toward the fixator 11 together with the retrieval device 20 or subsequent to the attachment of the retrieval device 20 with the engagement element 14. The operation of the catheter 26 has multiple facets. In one situation, the catheter 26 has an inner diameter being sufficiently small to prevent the windings of the coil 19 from travelling over the ridges 17 of the engagement element 14 and the unintended dislodging of the retrieval device 20 from the engagement element 14 without rotation. In a preferred embodiment, the coil 19 has an outer diameter of D, the coil wire has a diameter d and the height difference between a valley 13 and a neighbouring ridge 17 is h. The outer diameter of the engagement element 14 (projected on to a plane perpendicular to a longitudinal axis of the engagement element 14) is H. Thus, Thus, the inner diameter Dc of the catheter 26 then preferably is less than H+d. If d> h, a height of d−h of the wire extends above the ridges 17, whereby Dc preferably is less than H+2*d−h. In this manner, the catheter 26 will ensure that a wire winding of the retrieving device 20 is not able to travel over a ridge of the engagement 14.

Another operation of the catheter 26 is to push the catheter 26 over the engaging retrieving device 20 and engagement element 14 and to engage the basket 12. Further pushing the catheter 26 and/or pulling of the controlling device 22 may cause the basket 12 to collapse and move, with the engaging device 20 and element 14, into the catheter 26. The catheter 26 thus may be used as a "basket retrieval catheter" for retrieving the basket 12 and thus the fixator 11 for removal altogether from the body of the person or animal or for re-positioning the fixator 11 if desired.

Reverting to the operation of the retrieving device 20 and the engagement element 14, this is illustrated in more detail in FIG. 3 illustrating the engagement element 14 with the thread 15 with ridges 17 and valleys 13 spiralling along the longitudinal axis (same position as the guidewire 16 in this drawing) of the engagement element 14.

The valleys 13 are dimensioned to accommodate at least a part of the cross section of the wire used for the helical spring 19. A part of the wire may extend above or out of the valley 13 and above the neighbouring ridges 17. Also, the pitch of the engagement element 14, i.e. the width of a valley 13 and a ridge 17 corresponds to the pitch (diameter of the wire added the inter-winding distance) of the helical spring 19. In addition, the inner diameter of the spring 19 corresponds to the diameter of an imaginary cylinder defined by the lowest parts of the valleys, so that, in general, the spring 19 may be rotated into engagement with the engagement element 14 without unduly deforming the spring 19.

Naturally, a difference in pitch may be allowed, if the rotation is able to deform one or both threads to conform to the other.

The spring 19 has an end portion 21 where the wire has been cut, whereby this end portion 21 will extend in front of the remaining part of the spring 19. This end portion 21 will be curved (as the remainder of the coiled wire) and thus will resemble a type of hook.

Turning to the engagement element 14, this also has an end portion 23 where the interface between a valley 13 and a ridge 17 intersects the outermost portion of the element 14.

Clearly, when bringing the spring 19 to engage the element 14 while rotating the spring as illustrated (clockwise when viewing the spring 19 along the longitudinal axis (coinciding with the guidewire 16) from the right in the drawing), the protruding end portion 21 will engage the edge end portion 23 and thus guide the wire of the spring 19 into the groove 13' and thus initiate the engagement of the spring 19 and element 14.

Figure 6:
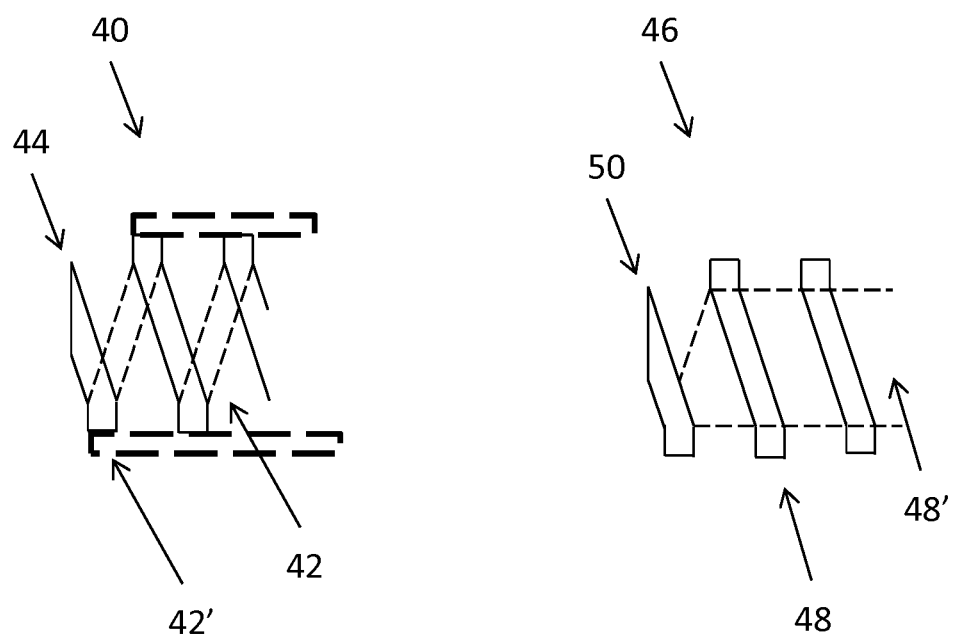

It is noted that attachment or engagement in FIGS. 3, 4, and 6 is performed by clockwise rotation of the spring, whereas it in FIGS. 2 and 5 is counterclockwise.

A stop portion 17' is illustrated which makes the helical ridge or groove 17 "blind" or proves a stop thereof, so that a tactile feedback may be provided to the operator or surgeon when rotating the spring 19 into engagement with the element 14. In one embodiment, the stop 17' further snap locks to the end portion 21, so that reverse rotation is only possible when a predetermined rotational force is exerted and so that accidental detachment between the coil 19 and the element 14 is avoided.

The advantage of the end portion 21 is that this extends farther than the remaining part of the spring 19 so that this engagement will take place even when the spring 19 and element 14 are not perfectly aligned as illustrated in the drawing.

In FIG. 4, the spring 19 of FIG. 3 has been rotated slightly, so that it is clear that the end portion 21 extends the pitch/lead distance from the neighbouring winding, whereby it forms a curved, extending portion 21 which may engage other elements such as the engagement element 14 even when an angle difference exist between these. If a flat surface is brought to engage the end portion 21, it may be tilted in any direction by an angle determined by the pitch distance and the diameter of the spring while only touching the end portion 21 and not other parts of the spring 19. Thus, this angle is the angle from which the spring 19 may contact the engagement element 14 without other parts of the spring 19 interacting and preventing the tip portion 21 from engaging the thread 15.

In FIG. 4, a line or plane (out of the plane of the drawing) 22 is seen between the tip or end portion 21 and an opposite (diametrically around the longitudinal axis) part 23. This line or plane 22 has an angle (indicated by the curved arrow) to the longitudinal axis of the spring 19. This angle explains how the protrusion protrudes from the remainder of the spring 19 and the manner in which this works to be able to engage with the thread of the element 14 without other parts of the spring 19 interfering.

In addition, illustrated is an element 24 which has a thread (not illustrated) and which is able to move into a space between the end portion 21 and the main part of the spring 19. The element 24 may be advanced until it engages the opposite part 23. It is seen that this is the situation even when there is an angle between the longitudinal axes of the spring 19 and the element 24. Thus, even in spite of this angular difference, the tip portion 21 will be able to engage the thread of the element 24.

If the tip portion 21 is kept in engagement with the thread of the element 24, relative rotation will bring the element 24 closer to the remainder of the spring 19.

If the guidewire 16 is further provided from the element 24 and through the spring 19, this reduction in space will also act to align the longitudinal axes of the element 24 and the spring, so that the remainder of the spring may engage the thread of the element 24.

Also helpful is the bendability of the spring 19 which preferably is fixed to a hollow catheter or the like for providing a rotational connection from an operator end thereof to the spring 19 and wherein the guidewire 16 may extend.

It is noted that the above operation of FIG. 4 is irrespective of whether the element 24 has an inner or outer thread.

This operation of the end portion 21 is further illustrated in FIG. 5.

In FIG. 5A, the engagement element 14 is illustrated with the guidewire 16. Again, it is noted that the guidewire 16 is fixed to an end portion of the element 14 so that the retrieving device 20 may be guided toward the element 14 using the guidewire 16.

In FIG. 5B, the retrieval device 20 with the spring 19 is pushed toward the engagement element 14 over the guidewire 16.

When the spring 19 engages the element 14, the end portion 21 will engage the element 14 while being rotated, whereby the end portion 21 will engage the thread 15 (see FIG. 3) of the element 14, and engagement by rotation may commence.

In FIG. 5C, the element 14 is illustrated positioned in a branch vessel 32 (c.f. FIG. 1), where the guidewire 16 makes a bend of more than 100 degrees through the main blood vessel and toward an arterial puncture (not illustrated) from which the guidewire 16 exits the person. The spring 19 is introduced along the guidewire and thus has to negotiate the sharp bend while being able to engage the element 14. However, the operation of the protruding end portion 21 combined with the bendability of the spring 19, which is desired in particular when this large bending angles are to be negotiated, will ensure that the bending allows the spring 19 to follow the guidewire 16 to a sufficient degree that the angular difference between the longitudinal axis at the spring end and the longitudinal axis of the element 14 is sufficiently low to be within the angular difference which the end portion 21 is capable of handling.

It is seen that the bendability of the spring 19, due to the interaction with the guidewire 16, brings the end portion 21 in engagement with the element 14 under an angle which is below that negotiable by the end portion 21. Clearly, the spring 19 may not align the end of the spring at the end portion 21 perfectly with the element 14, but the protruding and "catching" nature of the end portion 21 will ensure that the engagement is obtained nevertheless.

The presently preferred coil is a steel compression coil (EN 10270 Pt3. Aust. Stainless) of round wire of 0.32 mm thickness, a Youngs modulus (E) of 185000 N/mm$^2$ and a rigidity modulus (G) of 73000 N/mm$^2$. The coil has an outside diameter of 2.20 mm, inside diameter 1.56 mm, mean coil diameter 1.88 mm, solid length 19.52 mm, spring pitch 0.495 mm, helix angle 4.79°, 60 windings, a wire length of 355.61 mm, a spring rate of 0.240 N/mm, spring index 5.88. The tip portion 21 needs no particular treatment.

In the above, the retrieving device 20 has been illustrated as a coil 19. Naturally, other types of elements may be used instead, such as a bolt or other element, such as a special purpose element, a moulded element or the like, with an internal thread, preferably but not necessarily bendable. In FIG. 6, to the left, an element 40 is illustrated which may be a stiff or a flexible element and which has an outer wall 42', an inner thread 42 and a protruding part 44. To the right in FIG. 6, an element 46 is illustrated which again may be flexible or stiff and which has a core 48', an external thread 48 and a protruding element 50.

It is noted that the number of rotations required from initial engagement of the tip portion 21 with the valley 13 and until the stop 17' is engaged or the end of the element 14/valley 13 or the spring 19 has been reached, may vary from situation to situation. Presently, it is preferred that 3.5 windings are required, but this may vary from a fraction of a winding to tens of windings, if desired.

Naturally, the element 14 and the retrieval device 20 may have reversed functions, so that the element 14 has an internal thread and the device 20 an external thread. Actually, the coil 19 also has an external thread and thus may be equally well used with an element 14 with an internal thread.

The element 14 may be formed by any type of material and in any manner, such as moulding of a plastic material, a metal, or the like.

In order to facilitate the engagement between the device 20 and the element 14, the male element of these may be wedge-shaped or otherwise have a reduced cross section in the direction toward the female element, and/or the female element may be made funnel-shaped so as to more easily engage the male element.

The narrowing part of the male element and/or the funnel-shaped part of the female element may also be provided with threads in order to utilize a relative rotation there between to force the male element toward and into the female element.

It is noted that the present assembly may be used for numerous other manners of retrieval of devices, in addition to those seen in WO2012/065625 and US2012/0123510, such as filters, anchors, stents, grafts, a vena cava filter, an embolic protection device, a vascular occluding device, e.g. the amplatzer plug, a temporary anchored, hollow guidewire for local distribution of a drug, a valve replacement device in the treatment of cardiac valvular disease etc.

The invention claimed is:

1. An assembly of a retrieving element and a retrievable device, wherein:
    the retrievable device has one of a male element and a female element and
    the retrieving element has an other of the male element and the female element, where:
    the male element has a first outer surface defining a first thread having a predetermined direction of rotation around a longitudinal axis of the male element and
    the female element has a second inner surface defining a second thread configured to mate with the first thread, the second thread having a predetermined direction of rotation around a longitudinal axis of the female element, and
    wherein at least one of the male element and the female element has a main part and a protruding part protruding from the main part, the main part having the first outer surface or the second inner surface defining the pertaining first or second thread, the protruding part extending at least partly around the longitudinal axis of the pertaining male or female part and away from the main part, the direction of rotation of the protruding part being the same as the direction of rotation of the pertaining first or second thread of the pertaining male or female part,
    wherein the retrievable device comprises a guidewire attached at or to the retrievable device and extending through the retrieving element, the guidewire being configured to engage with an end of the retrievable device distal to the retrieving element such that the guidewire is prevented from being withdrawn from the retrievable device.

2. An assembly according to claim 1, wherein the male element has the protruding part and wherein the first outer surface extends no more than a first, predetermined distance from the longitudinal axis of the male element, and wherein the protruding part extends no more than the first predetermined distance from the longitudinal axis of the male element.

3. An assembly according to claim 1, wherein the female element has the protruding part and wherein the second inner surface extends at least a second, predetermined distance from the longitudinal axis of the female element, and wherein the protruding part extends at least the second predetermined distance from the longitudinal axis of the female element.

4. An assembly according to claim 1, wherein the protruding part has a tip portion, the tip portion and an outer part of the main part opposite, in relation to the longitudinal axis of the pertaining male or female part, to the tip portion define a line having an axis of no more than 80 degrees to the longitudinal axis of the pertaining male or female part.

5. An assembly according to claim 1, wherein the main part is bendable or flexible.

6. An assembly according to claim 1, wherein the protruding part has a surface part continuing the thread of the main part.

7. An assembly according to claim 1, wherein the at least one of the male and female element comprises a helical coil, the protruding part being a part of an extreme winding of the coil and the main part forming part of a central portion of the coil.

8. An assembly according to claim 7, the assembly further comprising a hollow, elongated element configured to receive therein the male and female elements, the female element comprising the helical coil, the helical coil being a coiled, elongate element having a predetermined, smallest diameter (d), the male element comprising the first thread with one or more groove(s) and one or more ridge(s), an inner diameter (Dc) of the hollow, elongate element smaller than the predetermined smallest diameter plus an outer diameter (H) of the male element, when projected on to a plane perpendicular to the longitudinal axis of the male element.

9. An assembly according to claim 7, the assembly further comprising a hollow, elongated element configured to receive therein the male and female elements, the female element comprising the helical coil, the helical coil being a coiled, elongate element having a predetermined, smallest diameter (d), the male element comprising the first thread with one or more groove(s) and one or more ridge(s), an inner diameter of the hollow, elongate element smaller than 2*d+H-h, where:
    d is the predetermined smallest diameter,
    h is a depth of the groove(s), and
    H is an outer diameter of the male element, when projected on to a plane perpendicular to the longitudinal axis of the male element.

10. An assembly according to claim 1, wherein the retrievable device comprises a compressible element configured to be provided inside a blood vessel of a person or animal.

11. An assembly according to claim 10, the assembly further comprising a hollow, elongated element configured to receive therein the male and female elements, the female element comprising a helical coil, the helical coil being a coiled, elongate element having a predetermined, smallest diameter (d), the male element comprising the first thread with one or more groove(s) and one or more ridge(s), an inner diameter (Dc) of the hollow, elongate element smaller than the predetermined smallest diameter plus an outer diameter (H) of the male element, when projected on to a plane perpendicular to the longitudinal axis of the male element.

12. An assembly according to claim 10, the assembly further comprising a hollow, elongated element configured to receive therein the male and female elements, the female element comprising a helical coil, the helical coil being a coiled, elongate element having a predetermined, smallest diameter (d), the male element comprising the first thread with one or more groove(s) and one or more ridge(s), an inner diameter of the hollow, elongate element smaller than 2*d+H-h, where:
  d is the predetermined smallest diameter,
  h is a depth of the groove(s), and
  H is an outer diameter of the male element, when projected on to a plane perpendicular to the longitudinal axis of the male element.

13. An assembly according to claim 1, wherein the male element has a reduced cross section in a direction toward the female element and/or the female element is funnel-shaped.

14. A method of operating the assembly according to claim 1, the method comprising:
  advancing the retrieving element toward the retrievable device,
  rotating the retrieving element in relation to the retrievable device to have the protruding part engage the thread of one of the male and female elements, and
  maintaining rotation to have the first and second threads engage.

15. A method according to claim 14, wherein the retrieving element comprises an opening through which the guidewire is translated to guide the retrieving element toward the retrievable element.

16. A method according to claim 14, wherein the advancing step comprises advancing the retrieving element until it abuts the retrievable device.

17. A method according to claim 14, wherein the step of maintaining rotation comprises maintaining the protruding part in engagement with the thread of the retrieving element/retrievable device that does not have the protruding part.

18. A method according to claim 14, wherein the rotating step comprises the protruding part griping or engaging an other of the male and female element that does not have the protruding part from an angle, between a longitudinal axis of the main part and the longitudinal axis of the other of the male and female element that does not have the protruding part, of at least 10 degrees.

19. An assembly of a retrieving element and a retrievable device, wherein:
  the retrievable device has one of:
    a male element having a first outer surface defining a first thread having a predetermined direction of rotation around a longitudinal axis of the male element,
    a helical coil having a second inner surface defining a second thread configured to mate with the first thread, the second thread having the predetermined direction of rotation around a longitudinal axis of the helical coil, and
  the retrieving element has an other of the male element and the helical coil,
  wherein the helical coil has a main part, forming a part of a central portion of the coil, and a protruding part of an extreme winding of the coil, the protruding part protruding from the main part, the main part having the first outer surface or the second inner surface defining the pertaining first or second thread, the protruding part extending at least partly around the longitudinal axis of the main part and away from the main part, a direction of rotation of the protruding part being the same as the direction of rotation of the pertaining first thread of the male element;
  the assembly further comprising a hollow, elongated element configured to receive therein the male element and the helical coil, the helical coil being a coiled, elongate element having a predetermined, smallest diameter, the first thread having one or more groove(s) and one or more ridge(s), an inner diameter of the hollow, elongate element being smaller than 2*d+H-h, where:
    d is the predetermined smallest diameter,
    h is a depth of the groove(s), and
    H is an outer diameter of the male element, when projected on to a plane perpendicular to a longitudinal axis of the male element,
  wherein the retrievable device comprises a guidewire attached at or to the retrievable device and extending through the retrieving element, the guidewire being configured to engage with an end of the retrievable device distal to the retrieving element such that the guidewire is prevented from being withdrawn from the retrievable device.

20. An assembly of a retrieving element and a retrievable device, wherein:
  the retrievable device has one of a male element and a female element and
  the retrieving element has an other of the male element and the female element,
  where:
    the male element has a first outer surface defining a first thread having a predetermined direction of rotation around a longitudinal axis of the male element; and
    the female element has a second inner surface defining a second thread configured to mate with the first thread, the second thread having the predetermined direction of rotation around a longitudinal axis of the female element, and
  wherein at least one of the male element and the female element has a main part and a protruding part protruding from the main part, the main part having the first outer surface or the second inner surface defining the pertaining first or second thread, the protruding part extending at least partly around the longitudinal axis of the pertaining male or female part and away from the main part, the direction of rotation of the protruding part being the same as the direction of rotation of the pertaining first or second thread of the pertaining male or female part,
  wherein the retrievable device comprises a guidewire attached at or to the retrievable device and extending through the retrieving element, the guidewire being configured to engage with an end of the retrievable device distal to the retrieving element such that the guidewire is prevented from being withdrawn from the retrievable device.

21. The assembly of claim 20, wherein the retrievable element is one of an intravascular filter, an anchor, a dilator, a stent or a graft.

22. The assembly of claim 20, wherein the retrievable element is configured to temporarily fix itself to a blood vessel.

* * * * *